US011324463B1

(12) United States Patent
Helm et al.

(10) Patent No.: US 11,324,463 B1
(45) Date of Patent: May 10, 2022

(54) FILTER SYSTEM AND METHOD FOR IMAGING A SUBJECT

(71) Applicant: Medtronic Navigation, Inc., Louisville, CO (US)

(72) Inventors: Patrick A. Helm, Milton, MA (US); Seunghoon Nam, Bedford, MA (US); Shuanghe Shi, Southborough, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 17/080,423

(22) Filed: Oct. 26, 2020

(51) Int. Cl.
*A61B 6/00* (2006.01)
*G06T 11/00* (2006.01)
*A61B 6/03* (2006.01)

(52) U.S. Cl.
CPC ............ *A61B 6/4035* (2013.01); *A61B 6/032* (2013.01); *A61B 6/4291* (2013.01); *G06T 11/005* (2013.01)

(58) Field of Classification Search
CPC ..... A61B 6/4035; A61B 6/032; A61B 6/4291; G06T 11/005
See application file for complete search history.

(56) References Cited

U.S. PATENT DOCUMENTS

| | | | |
|---|---|---|---|
| 8,238,631 B2 | 8/2012 | Hartmann et al. | |
| 2008/0198963 A1 | 8/2008 | Spahn | |
| 2010/0290690 A1 | 11/2010 | Hartmann et al. | |
| 2012/0069953 A1 | 3/2012 | Chandra et al. | |
| 2012/0076258 A1 | 3/2012 | Chandra et al. | |
| 2012/0097178 A1 | 4/2012 | Helm et al. | |
| 2012/0099768 A1 | 4/2012 | Helm et al. | |
| 2012/0099772 A1 | 4/2012 | Helm et al. | |
| 2012/0250822 A1 | 10/2012 | Helm et al. | |
| 2015/0170359 A1* | 6/2015 | Star-Lack | G06T 7/0012 382/131 |
| 2015/0182179 A1 | 7/2015 | Edic et al. | |
| 2015/0272522 A1 | 10/2015 | Robinson et al. | |
| 2016/0354046 A1* | 12/2016 | Freudenberger | A61B 6/4291 |
| 2018/0310899 A1 | 11/2018 | Garlow et al. | |
| 2020/0069271 A1 | 3/2020 | Maalej et al. | |

FOREIGN PATENT DOCUMENTS

KR    20190140641 A    12/2019

OTHER PUBLICATIONS

U.S. Appl. No. 17/080,398, filed Oct. 26, 2020, Helm, et al.
International Search Report and Written Opinion regarding International Patent Application No. PCT/US2021/056664, dated Feb. 4, 2022.
Ho Lee et al: "Binary moving-blocker-based scatter correction in cone-beam computed tomography with width-truncated projections: proof of concept", Physics in Medicine and Biology, Institute of Physics Publishing, Bristol GB, vol. 62, No. 6, Feb. 21, 2017 (Feb. 21, 2017).
International Search Report and Written Opinion regarding International Application No. PCT/US2021/056682, dated Feb. 7, 2022.

* cited by examiner

*Primary Examiner* — Courtney D Thomas
(74) *Attorney, Agent, or Firm* — Harness, Dickey & Pierce, P.L.C.

(57) ABSTRACT

A method and system is disclosed for acquiring image data of a subject. The image data can be collected with an imaging system with a selected filtering characteristic. The image data can be reconstructed using reconstruction techniques.

17 Claims, 7 Drawing Sheets

FILTER SYSTEM AND METHOD FOR IMAGING A SUBJECT

CROSS-REFERENCE TO RELATED APPLICATIONS

This application includes subject matter similar to that disclosed in concurrently filed U.S. patent application Ser. No. 17/080,398. The entire disclosure of which is incorporated herein by reference.

FIELD

The present disclosure relates to imaging a subject, and particularly to a system to acquire image data with a selected filter system.

BACKGROUND

This section provides background information related to the present disclosure which is not necessarily prior art.

A subject, such as a human patient, may undergo a surgical procedure to address an issue in the subject's anatomy. The surgery can include various procedures, such as movement or augmentation of bone, insertion of an implant (i.e. an implantable device), or other appropriate procedures.

Images of a subject can assist a surgeon in planning and performing a procedure. A surgeon may select a two-dimensional image or a three-dimensional image representation of the subject, based on images acquired from an imaging system, such as a magnetic resonance imaging (MRI) system, computed tomography (CT) system, fluoroscopy (e.g. C-Arm imaging systems), or other appropriate imaging systems. The images can assist the surgeon in performing a procedure with less invasive techniques by allowing the surgeon to view the anatomy of the subject without removing the overlying tissue (including dermal and muscular tissue).

SUMMARY

This section provides a general summary of the disclosure and is not a comprehensive disclosure of its full scope or all of its features.

According to various embodiments, an imaging system acquires image data of a subject, such as a living patient (e.g., a human patient). Imaging systems may acquire image data at a plurality of energies. Imaging systems may also include filter members alternatively to or in addition to multiple energy emission systems. The filters may augment or select a beam or emission (e.g., x-ray beam) for generating image data, such as with projections of the subject. Imaging systems may include those disclosed in U.S. Pat. App. Pub. No. 2018/0310899, published Nov. 1, 2018, and entitled "FILTER SYSTEM AND METHOD FOR IMAGING A SUBJECT", incorporated by reference herein.

Enhanced or selected contrast imaging can include a contrast agent injected and/or applied to the subject used either with one and/or the plurality of energies. Also, various filters may be used at selected times alone or in combination with the contrast agent. Thus, a plurality of image projections may be acquired with or without the contrast agent and/or with or without a selected one or more filters.

An imaging system having a plurality of energies may include portions that operate at different parameters allow for emission of multiple beams with differing characteristics. Thus, the beam may have characteristics based on selected parameters and/or have selected energy parameters. In various embodiments, the imaging system may include a first energy source with one or more first energy parameters and one or more second energy source with a second energy parameters to energize a source. Further, the imaging system may include a plurality of sources (each source may have the same trajectory or path), wherein each source includes one or more different features or portions to achieve the first and second energy parameters (e.g., voltage) to provide emitted beams (e.g., of X-rays) with the different energy characteristics.

The imaging system with filters may include one or more filters to ensure, and/or assist in ensuring, appropriate or selected separation between the first energy characteristics and the second energy characteristics. The first energy characteristics may be selected to provide a first x-ray energy spectra with the first energy characteristics and a second x-ray energy spectra at the second energy characteristics. The filter may be provided at a selected time to assist in ensuring appropriate or selected spectra for imaging the subject, such as eliminating possible or actual overlap of the x-ray energy spectra.

One or more filters may also be used to various purposes in acquiring selected image projections. The filters may be used to generate a plurality of image projections with a single broad spectrum beam. Selected filters may also be used to assist in detecting and/or correcting for various aberrations and/or distortions.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
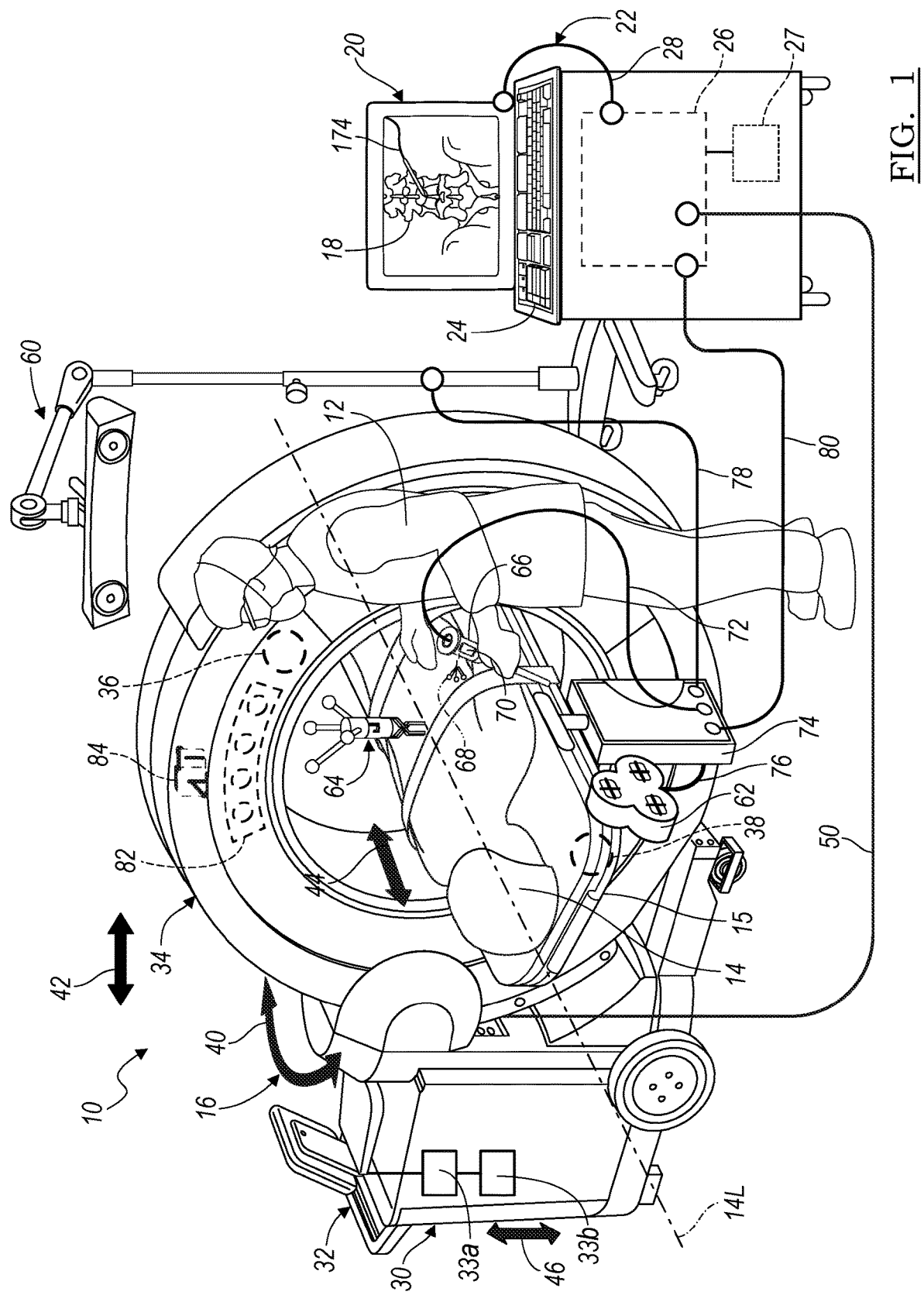
FIG. 1 is an environmental view of an imaging system in an operating theatre.

With reference to FIG. 1, in an operating theatre or operating room 10, a user, such as a surgeon 12, can perform a procedure on a subject, such as a patient, 14. In performing the procedure, the user 12 can use an imaging system 16 to acquire image data of the patient 14 to allow a selected system to generate or create images to assist in performing a procedure. A model (such as a three-dimensional (3D) image) can be generated using the image data and displayed as an image 18 on a display device 20. The display device 20 can be part of and/or connected to a processor system 22 that includes an input device 24, such as a keyboard, and a processor module 26 which can include one or more processors or microprocessors (e.g., central processing units, graphics processor units, etc.) incorporated with the processing system 22 along with selected types of non-transitory and/or transitory memory module 27. A connection 28 can be provided between the processor 26 and the display device 20 for data communication to allow driving the display device 20 to display or illustrate the image 18.

The imaging system 16 can include an O-Arm® imaging system sold by Medtronic Navigation, Inc. having a place of business in Louisville, Colo., USA. The imaging system 16, including the O-Arm® imaging system, or other appropriate imaging systems may be in use during a selected procedure, such as the imaging system described in U.S. Patent App. Pubs. 2012/0250822, 2012/0099772, and 2010/0290690, all incorporated by reference herein.

The imaging system 16 may include a mobile cart 30. The imaging system 16 may further include a controller and/or control system 32. In various embodiments, the controller 32 may be incorporated in the mobile cart 30 if present. The control system may include a processor module 33a and a memory module 33b (e.g., a tangible, non-transitory memory). The memory 33b may include various instructions that are executed by the processor 33a to control the imaging system, including various portions of the imaging system 16. The control system may include a processor such as a general purpose processor or a specific application processor and a memory system (e.g., a tangible, non-transitory memory, such as a spinning disk or solid state non-volatile memory). For example, the memory system may include instructions to be executed by the processor to perform functions and determine results, as discussed herein.

The imaging system 16 may further include an imaging gantry 34 in which is positioned a source unit 36 and a detector 38. The gantry 34 may be connected to the mobile cart 30. The gantry may be O-shaped or toroid shaped, wherein the gantry is substantially annular and includes walls that form a volume in which the source unit 36 and detector 38 may move.

The mobile cart 30 can be moved from one operating theater to another and the gantry 34 can move relative to the cart 30, as discussed further herein. This allows the imaging system 16 to be mobile and moveable relative to the subject 14. Thus, the imaging system 16 may be used in multiple locations and with multiple procedures without requiring a capital expenditure or space dedicated to a fixed imaging system.

The source unit 36 may be an x-ray emitter that can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed (such as with a fixed inner gantry or moving system) to the detector 38. Also, the gantry 34 can move isometrically relative to the subject 14, which can be placed on a patient support or table 15, generally in the direction of arrow 40 as illustrated in FIG. 1. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

The source 36, as discussed herein, may include one or more sources of x-rays for imaging the subject 14. In various embodiments, the source 36 may include a single source that may be powered by more than one power source to generate and/or emit x-rays at different energy characteristics. Further, more than one x-ray source may be the source 36 that may be powered to emit x-rays with differing energy characteristics at selected times. Dual energy imaging systems may include those disclosed in U.S. Pat. App. Pub. Nos. 2012/0099768 and 2012/0097178, both incorporated herein by reference.

According to various embodiments, the imaging system 16 can be used with an un-navigated or navigated procedure. In a navigated procedure, a localizer and/or digitizer, including either or both of an optical localizer 60 and an electromagnetic localizer 62 can be used to generate a field and/or receive and/or send a signal within a navigation domain relative to the patient 14. The navigated space or navigational domain relative to the patient 14 can be registered to the image 18. Correlation, as understood in the art, is to allow registration of a navigation space defined within the navigational domain and an image space defined by the image 18. A patient tracker or dynamic reference frame 64 can be connected to the patient 14 to allow for a dynamic registration and maintenance of registration of the patient 14 to the image 18.

The patient tracking device or dynamic registration device 64 and an instrument 66 can then be tracked relative to the patient 14 to allow for a navigated procedure. The instrument 66 can include a tracking device, such as an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation/probe interface device 74 such as the electromagnetic localizer 62 with communication line 76 and/or the optical localizer 60 with communication line 78. Using the communication lines 74, 78 respectively, the interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of a tracked location of the instrument 66 relative to the image 18 for performing a procedure.

One skilled in the art will understand that the instrument 66 may be any appropriate instrument, such as a ventricular or vascular stent, spinal implant, neurological stent or stimulator, ablation device, or the like. The instrument 66 can be an interventional instrument or can include or be an implantable device. Tracking the instrument 66 allows for viewing a location (including x,y,z position and orientation) of the instrument 66 relative to the patient 14 with use of the registered image 18 without direct viewing of the instrument 66 within the patient 14.

Further, the gantry 34 can include an optical tracking device 82 or an electromagnetic tracking device 84 to be tracked with the respective optical localizer 60 or electromagnetic localizer 62. Accordingly, the imaging device 16 can be tracked relative to the patient 14 as can the instrument 66 to allow for initial registration, automatic registration, or continued registration of the patient 14 relative to the image 18. Registration and navigated procedures are disclosed in U.S. Pat. No. 8,238,631, incorporated herein by reference. Upon registration and tracking of the instrument 66, an icon 174 may be displayed relative to, including superimposed on, the image 18. Briefly, registration includes a transformation of image space and patient space to allow for illustration of a tracked object (e.g. the instrument 66) relative to (e.g. superimposed on) the image 18.

Figure 2:
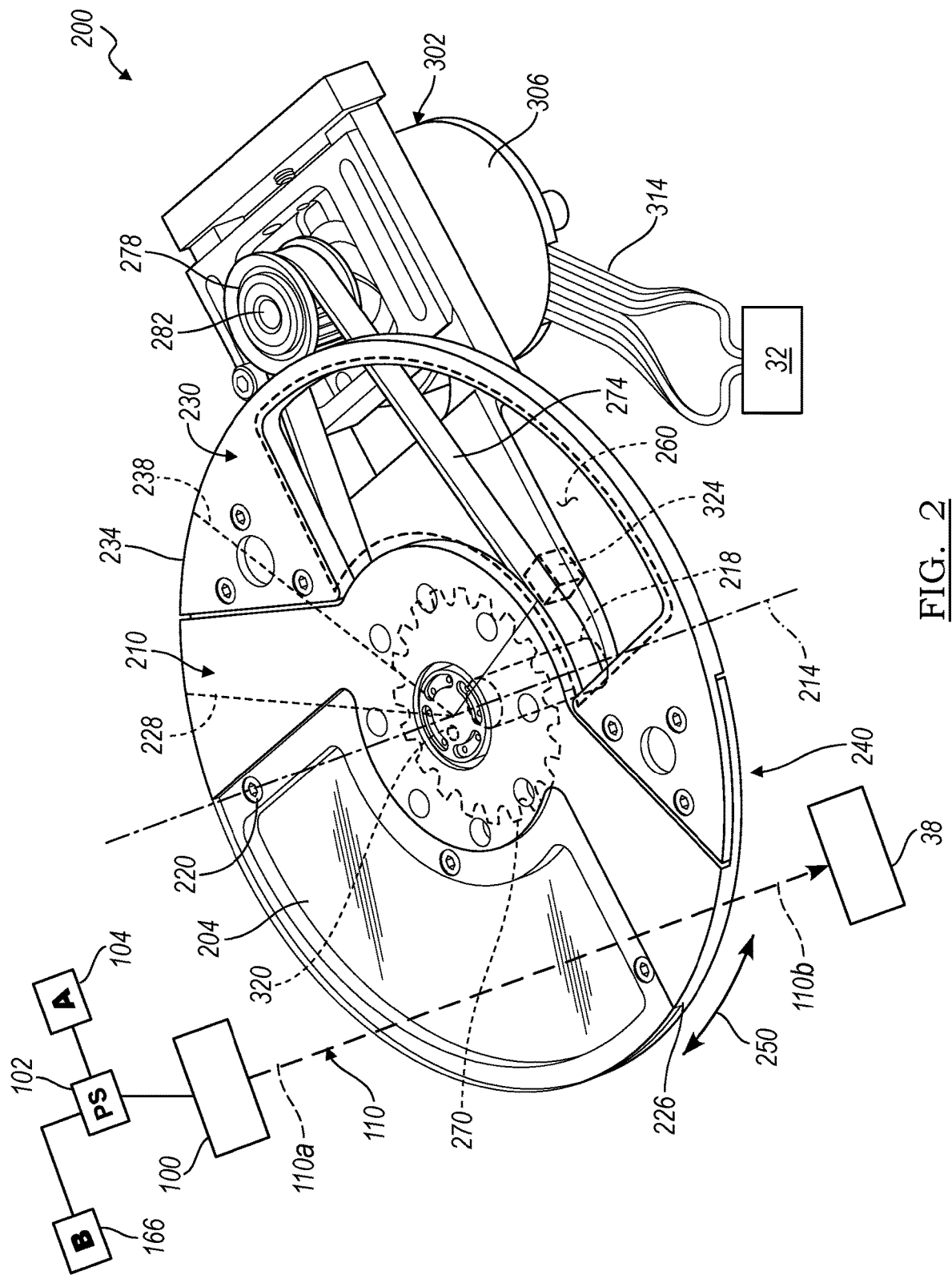
FIG. 2 is a schematic illustration of a filter assembly, according to various embodiments.

Turning reference to FIG. 2, according to various embodiments, the source 36 can include a single x-ray tube 100 that can be connected to a switch 102 that can interconnect a first power source A 104 and a second power source B 106 with the x-ray tube 100. X-rays can be emitted from the x-ray tube 100 in a selected shape or configuration, such as a cone shape, that may be centered about a ray or line 110 directed toward the detector 38. The switch 102 can switch between the power source A 104 and the power source B 106 to power the x-ray tube 100 at different power parameters, such as selected and different voltages and/or amperages to emit x-rays at different energy characteristics generally in the direction of the vector 110 towards the detector 38. The vector 110 may be a central vector or ray within the beam of x-rays. The vector 110 may include a selected line or axis relevant for further interaction with the beam, such as with a filter member, as discussed further herein.

It will be understood, however, that the switch 102 can also be connected to a single variable power source that is able to provide power characteristics at different voltages and/or amperages rather than the switch 102 that connects to two different power sources A 104 and B 106. Also, the switch 102 can be a switch that operates to switch a single power source between different voltages and amperages. Further, the source 36 may include more than one source that is configured or operable to emit x-rays at more than one energy characteristic. The switch, or selected system, may operate to power the two or more x-rays tubes to generate x-rays at selected times.

The patient 14 can be positioned within the x-ray beam to allow for acquiring image data of the patient 14 based upon the emission of x-rays in the direction of vector 110 towards the detector 38.

Acquisition of projections with beams (e.g., x-rays beams) at more than one power or energy characteristic (e.g. dual power characteristics) may allow for enhanced and/or dynamic contrast reconstruction of models of the subject 14 based upon the image data acquired of the patient 14. It is understood, however, that more than two power sources may be provided or they may be altered during operation to provide x-rays at more than two energy characteristics. In addition and/or alternatively to more than one source and/or power source, a filter assembly 200 may be provided to assist in and/or generation of acquisition of projections at multiple power parameters. The discussion herein of two or dual energy is merely exemplary and not intended to limit the scope of the present disclosure, unless specifically so stated.

Further, one or more models may be generated with one or more projections with the imaging system 16. The processor module 24, 33*a* may execute selected instructions to generate the models. The instructions may include an iterative or algebraic process can be used to reconstruct the model (such as for the image 18) of at least a portion of the patient 14 based upon the acquired image data. It is understood that the model may include a three-dimensional (3D) rendering of the imaged portion of the patient 14 based on the image data. The rendering may be formed or generated based on selected techniques, such as those discussed herein.

The x-ray tube 100 may be used to generate two dimension (2D) x-ray projections of the patient 14, selected portion of the patient 14, or any area, region or volume of interest. The 2D x-ray projections can be reconstructed, as discussed herein, to generate and/or display three-dimensional (3D) volumetric models of the patient 14, selected portion of the patient 14, or any area, region or volume of interest. As discussed herein, the 2D x-ray projections can be image data acquired with the imaging system 16, while the 3D volumetric models can be generated or model image data.

For reconstructing or forming the 3D volumetric image, appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to perform a 3D volumetric reconstruction based on the 2D projections allows for efficient and complete volumetric reconstruction. Generally, an algebraic technique can include an iterative process to perform a reconstruction of the patient 14 for display as the image 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The 2D projection image data can be acquired by substantially annular or 360° orientation movement of the source/detector 36/38 around the patient 14 due to positioning of the source/detector 36/38 moving around the patient 14 in the optimal movement. An optimal movement may be a predetermined movement of the source/detector 36/38 in a circle alone or with movement of the gantry 34, as discussed above. An optimal movement may be one that allows for acquisition of enough image data to reconstruct a select quality of the image 18. This optimal movement may allow for minimizing or attempting to minimize exposure of the patient 14 and/or the user 12 to x-rays by moving the source/detector 36/38 along a path to acquire a selected amount of image data without more or substantially more x-ray exposure.

Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

In acquiring image data at the detector 38, the selected energy x-rays generally interact with a tissue and/or a contrast agent in the patient 14 differently based upon the characteristics of the tissue or the contrast agent in the patient 14 and the energies of the two x-rays emitted by the x-ray tube 100. For example, the soft tissue of the patient 14 can absorb or scatter x-rays having a first energy differently than the x-rays having a second energy different than the first energy. Similarly, a contrast agent, such as iodine, can absorb or scatter the x-rays at the first energy differently from those at the second energy. Different energy x-rays may be used to distinguish and/or differentiate different types of material properties (e.g. hard or soft anatomy or between two types of soft anatomy (e.g. vessels and surrounding tissue)), contrast agent, implants (e.g. metal implants) and surrounding natural anatomy (e.g. bone), or etc. within the patient 14. By switching between two or more power parameters and knowing the time to generate the x-rays the information detected at the detector 38 can be used to identify or segregate the different types of anatomy or contrast agent being imaged.

At least because the x-ray tube 100 is in a moveable imaging system, such as the imaging system 16, it can be moved relative to the patient 14. Thus, the x-ray tube 100 may move relative to the patient 14 while the energy of the x-rays that reach or are attenuated by the subject 14 is being changed or altered. Accordingly, an image projection acquired with the first energy may not be at the same pose or position relative to the patient 14 as the second energy. If the model is desired or selected to be formed of a single location in the patient 14, however, various interpolation techniques can be used to generate the model. Interpolation may occur between image data acquired at a first time and image data acquired at a second time. The image data at the first and second times may be generated with the two different energies. Thus, the model may be formed including image data from both energies using interpolation between the acquired image data. Further, the interpolation may be to account for an amount of movement (e.g. linear, rotational, etc.) of the x-ray tube 100 between when the projection is generated with the first energy and the projection is generated with the second energy. Accordingly, a projection regarding a single pose may be generated with two energies via interpolation that accounts for movement of the source 100 during image acquisition.

In addition to and/or alternatively to the generation of x-rays at different energies from one or more sources, the filter assembly 200 can be used to assist in insuring or creating a select differentiation between x-ray spectras of x-rays of the two different energies. Filter assemblies that may be appropriate include those disclosed in U.S. Pat. App. Pub. No. 2018/0310899, published Nov. 1, 2018 and entitled "FILTER SYSTEM AND METHOD FOR IMAGING A SUBJECT", incorporated by reference herein. The filter assembly 200 may be operated in a selected manner, such as an interval manner that may be timed and/or gated to relate to various parameters including the image acquisition as discussed above. Therefore, the filter assembly 200 can be operated to image the patient 14 to achieve the differentiation between the dual energies of the x-rays.

Turning reference to FIG. 2, the filter assembly 200 is illustrated. The filter assembly 200 may include a filter member 210 that is carried by a filter carrier 210, wherein the filter carrier 210 may rotate around an axis 214 on a shaft 218. The filter member 204 may be formed of a selected material, including those that selectively attenuate x-rays including lead, aluminum, tin, etc., and fixed to the filter carrier 210. The first filter 204 may block or limit selected x-ray photons related to selected energies of a broad spectrum beam, as discussed herein.

The first filter member 204 may be fixed or held with the carrier in selected manners such as, bores may be formed in the filter member 204 and one or more screws 222 fix the filter member 204 to the filter carrier 210 by passing through or engaging the filter member 204 and the filter carrier 210. It is understood that other fixation mechanisms may be provided, such as welding, adhesives, brazing, or the like, to fix the filter member 204 to the filter carrier 210. The carrier 210 may further be provided as a frame such that x-rays that pass through the filter member 204 and reach the detector 38 pass through the filter member 204, but not the material of the filter carrier 210.

As illustrated in FIG. 2, the filter carrier 210 may have a curved outer edge 226 such that the filter carrier 210 includes a radius 228 and has an outer arcuate edge 226. The filter carrier 210, therefore, may form at least a part of a circle or round member. The combination of the filter carrier 210 and the filter member 204 may have a selected mass that defines or forms only a portion of a circle. Therefore, a counterbalance 230 may be fixed to the filter carrier 210 to counter balance the mass of the filter member 204 and the filter carrier 210.

The counterbalance may have an arcuate outer edge 234 and a substantially similar radius 238 to the radius 228. The counter balance 230, therefore, may form a circle with the filter carrier 210. The counterbalance 230 and the filter carrier 210 form a filter carrier assembly 240 to move the filter member 204 relative to the x-ray to be positioned into or out of the x-rays generally travelling along the direction 110, as schematically illustrated in FIG. 2.

In various embodiments, the filter carrier 210 may include a second filter member or material 260. The second filter 260 may block or limit selected x-ray photons related to selected energies of a broad spectrum beam, as discussed herein. The second filter may be placed in a selected position relative to the first filter 204. The second filter 260 may be in place of or positioned as the counterbalance 230 to the first filter 204. As the filter carrier 210 rotates, therefore, the second filter 260 may also be placed in the beam 110.

The filter carrier 210 may rotate around the shaft 218 that has or forms the central axis 214. The filter carrier 210 may be operated to rotate in two directions or in a single direction, such as in the direction of arrow 250 around the axis 214. In various embodiments, the filter carrier 210 may be moved to carry the filter member 204 in substantially one rotational direction.

According to various embodiments, the filter carrier 210 may be operated to rotate around the axis 214 at a selected rate. The selected rate may be a substantially constant speed and rotation per minute (RPM) and/or changeable for a selected period of time. Therefore, whether the filter member 204 is in the beam path 110, the second filter 260, and/or a selected open area (e.g., no filter) may be in the beam path 110. In various embodiments, a selected portion of the filter assembly 200 may be placed in the beam 110 every about 33 milliseconds.

In various embodiments, the filter carrier assembly 210 may be connected to a carry gear 270. The carry gear 270, in various embodiments, is driven by a belt 274 that is driven by a drive gear 278 that is connected to a shaft 282 powered by a motor assembly 302. The motor assembly 302 may include a housing 306 and a powered motor (not specifically illustrated) within the housing 306. The motor assembly 302 may be powered by various power mechanisms, such as electrical power, pneumatic power, or the like. The motor assembly 306 may be any appropriate motor assembly that can drive the filter carrier assembly 210 at the selected speed and be powered by the imaging system 16 and controlled by the controller 32. The motor assembly 306 may include an appropriate stepper and/or servo motors, for example the Maxon® EC-I-40 brushless DC servo motor sold by Maxon Motor Ag having a place of business in Switzerland.

Control connection 314 may be provided and interconnected with the imaging system controller 32. As discussed above, the positioning of the filter member 200 may be controlled by the imaging system controller 32 to filter x-ray spectra, as discussed above. The filter member carrier assembly 210 may be mounted to the carry gear 270 through the appropriate mechanism, such as one or more screws, bolts, adhesives, rivets, or other appropriate mechanical or chemical adhesions of the carrier assembly 210 to the carry gear 270. Therefore, upon rotation of the drive gear 278 the belt 274 may drive the carry gear 270 to spin the filter carrier assembly 210, including the filter members 204, 260, at a selected rotation rate. It is understood, however, that the motor assembly 302 may be directly connected to the carry gear 270 without requiring the belt 274. In a direct connection, for example, the carry gear 270 may be mounted directly to the shaft 282 (e.g. replacing the drive gear 278) and/or the carry gear 270 may directly engage the drive gear 278 without the belt 274 and/or other transmission system. Alternatively, other appropriate drive or transmission mechanisms may be provided between the drive gear 278 and the carry gear 270 such as a worm drive, a geared transmission, or other appropriate connection systems.

During operation, the position of the filter member 200 may be synced with the location of the beam 110 in time with the emission of the x-rays at the selected power that are intended or selected to pass through the filter members 204, 260 before reaching the patient 14. According to various embodiments, the filter assembly 200 may include an encoder assembly. The encoder assembly may be used to sense, determine, and/or transmit a position of the filter carrier 210 to the control 32 or other appropriate controller. In various embodiments, the encoder may include various components such as a magnetic member 320 positioned on the carrier 210 and a sensor (e.g. a Hall Effect sensor) 324 positioned to sense movement of the magnetic member 320. The encoder may include those disclosed in U.S. Pat. App. Pub. No. 2018/0310899, published Nov. 1, 2018 and entitled "FILTER SYSTEM AND METHOD FOR IMAGING A SUBJECT", incorporated by reference herein.

With continuing reference to FIG. 2 and additional reference to FIG. 3, the imaging system 16 may be used to generate projections of the patient 14 with one or a plurality of energies at the detector 38. In particular, energies of a beam, such as an x-ray beam traveling along the path of the ray 110, may impinge or reach the detector 38 and/or the patient 14 at discrete and selected energies. For example, the beam that travels along the path 110 through the patient 14 to the detector 38 may be selected to be at least at two different energies. The two energies may be separated by a selected amount, as discussed herein.

In various embodiments, for example, the source 36 at the x-ray tube 100 may transmit or emit a broad spectrum beam, such as an x-ray beam, with many different energy levels which includes a board energy spectrum. For example, the beam emitted by the tube 100 may emit a beam 110a in the direction of the ray 110 to include a spectrum of energies (e.g., about 40 keV to about 140 keV), with peak energies of including about 50 kVp to about 200 kVp, including about 80 kVp to about 140 kVp. At each of the peak energies, it is understood, however, that a range of energy in a spectra may include the peak value. The beam 110a, however, may be selectively altered and/or filtered.

The beam 110a, as schematically illustrated in FIG. 2, is emitted from the tube 100. As the beam passes through the filter assembly 200, it may engage the first filter 204 and/or the second filter 260. The beam 110a, therefore, may be attenuated by the two filters 204, 260. In various embodiments, the two filters may limit or attenuate the beam 110a to two different energies in a post-filtered beam portion 110b. Accordingly, the beam 110a may include a pre-filter portion 110a and the second filter portion or post-filter portion 110b. The post-filter portion 110b may have two distinct energies depending upon which filter it is passed through.

Figure 3A:
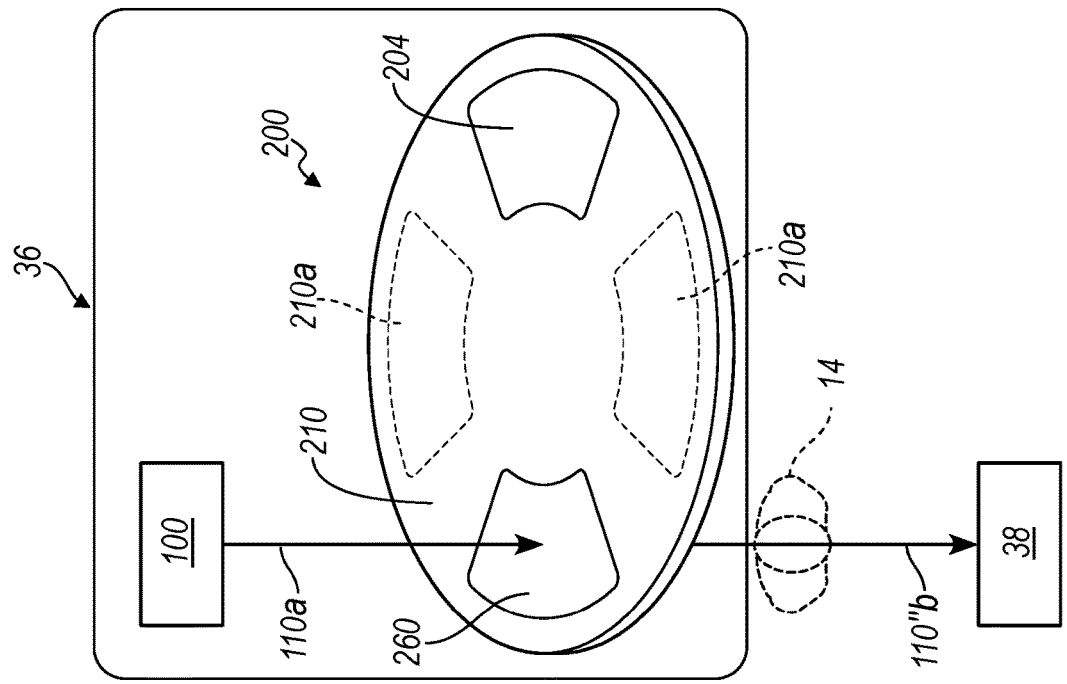
FIGS. 3A and 3B are schematic illustrations of an imaging system including a source assembly, filter assembly, and detector, according to various embodiments.
Figure 3B:
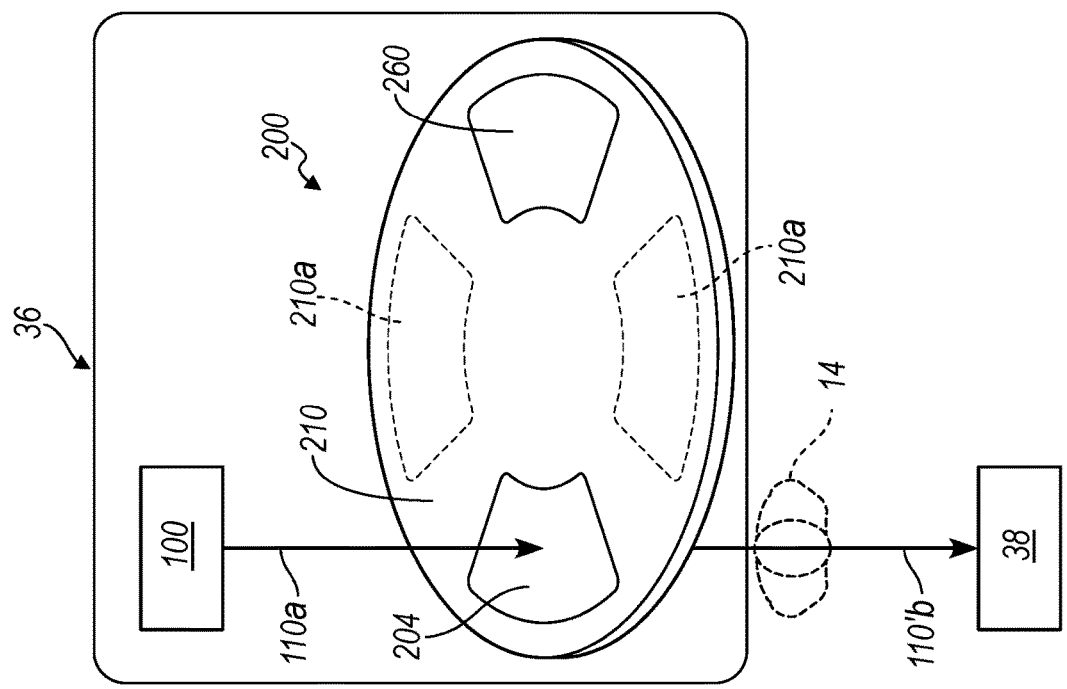

As schematically illustrated in FIGS. 3A and 3B, the pre-filter beam 110a may be a broad spectrum beams and may have a selected energy range or spectrum, such as that discussed above. The post-filter beam 110b that passes through the first filter 204 may have a first beam spectra where low-energy x-ray are attenuated and thus increasing the Half-Value Layer (HVL) which may also alter the kVp of the post-filter beam. With reference to FIG. 3A, the first filter 204 may filter the broad spectrum pre-filter beam portion 110a to a first selected post-filter spectrum 110b' that may also be referred to as a partial or limited beam.

Turning reference to FIG. 3B, the second filter 260 may filter the broad spectrum pre-filter beam 110a to a second selected post-filter beam 110b". The second post-filter beam 110b" may include a selected power characteristic, such as a separate or different spectra or voltage, from the first post-filter beam 110b' and may also have a differing HVL. The second post-filter beam energy 110b", which may also be referred to as a limited or partial beam, may have a second post-filter beam spectra with a higher HVL than the first post-filter beam.

Thus, the first and second post-filter beams may have differing peak energies, such as differing by about 40 kVp to about 80 kVp, where each beam may be selected from a range of about 40 kVp to about 200 kVp. Each selected kVp, however, may have a known or understood spread around to the kVp. Further, the HVL may be different between the first and second post-filter beams. For example, the HVL may differ by about 2 millimeters of Aluminum (mm Al) to about 8 mm Al, and HVL values for each beam may be selected from about 1 mm Al to about 15 mm Al, including about 2 mm Al to about 10 mm Al. It is understood by one skilled in the art that the HVL is an equivalent thickness of Aluminum (Al) that reduces a beam intensity by one-half.

As illustrated in FIGS. 3A and 3B, the filter carrier 210 may also define one or more openings or passages 210a. The openings may allow for passage of an unfiltered or broad spectrum beam for image collection and/or other purposes.

Thus, image data may be acquired with one or more filter arrangements and/or an open (i.e., broad spectrum beam image data acquisition).

As illustrated in FIGS. 3A and 3B, both of the post-filter beams 110b may reach the detector 38. In both instances, however, the post-filter beam 110b may pass through and/or be attenuated by the subject 14. Accordingly, as both of the post-filter beams 110b', 110b" include different energies or power characteristics that are attenuated by the patient 14 and reach the detector 38 the projectors received or determined with the detector 38 may be based upon different beam energies. Therefore, although the single pre-filter beam 110a may be emitted by the source 36, including the x-ray tube 100, the beam attenuated or reaching the subject 14 may be differentiated into at least two different beams. The two different energies of the two different post-filter beams 110b', 110b" may be used to differentiate and/or distinguish various features in the patient 14 in the image data collected at the detector 38 as discussed above. The single source tube and a single pre-filter beam 110a, however, may be used to generate the two post-filter beams with different energies 110b', 110b". The filter assembly 200 including the two filter members 204, 260 may be used to generate the two different post-filter beams 110b', 110b". It is further understood, however, that the filter assembly may include more than two filters and/or an open area that allow for generation of more than two energies and/or to allow the whole broad spectrum beam to pass in the path 110 for image data acquisition.

Figure 4:
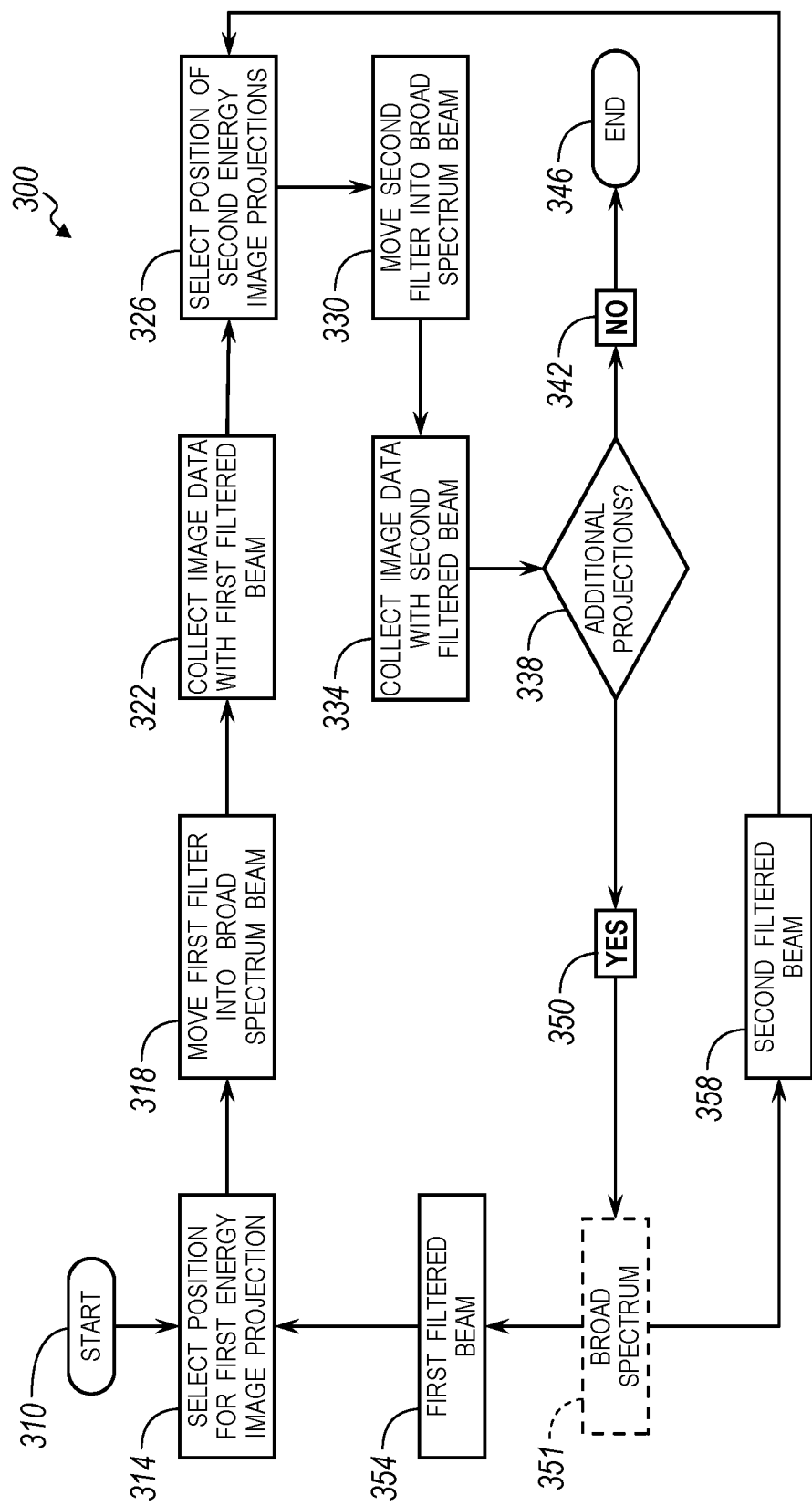
FIG. 4 is a flow chart of a method of operating an imaging system with a filter assembly.

The image acquisition or image data acquisition of the subject 14 at the detector 38, therefore, may proceed in a selected manner, such as according to a method 300 as illustrated in FIG. 4. The method 300 may be used to acquire image projections or image data of the subject 14 at two different energies or power characteristics of the beam 110a from the single source tube 100 and the single broad spectrum beam 110a. The method may start in block 310 which may include positioning the subject 14 relative to the imaging system 16, moving the imaging system 16 relative to the subject, or other appropriate procedures.

The method 300 may be used to collect image data of the subject 14 with either the first post-filter beam 110b' or the post-second filter beam 110b". It is understood, however, that additional filters may be provided and, therefore, additional or more than two post-filter beams with different and distinguishable energies may also be produced. Further, although the method herein illustrates and refers to the use of the two filters 204, 260, it is understood that only a single filter may be used to collect all projections of the subject 14 and/or only two filters may be selected out of a plurality of filters, for operation of the imaging system 16. Accordingly, the discussion herein of using the two filters 204, 260 is merely exemplary for including a plurality of filters to achieve a plurality of post-filtered beam energy for collection of a plurality of image data of the subject 14.

Accordingly, the method 300 after the start in block 310 may include selecting a position for the first energy image projection in block 314. For example, the image assembly 16 can include rotation of the source 36 relative to the subject 14 and/or other movements of the gantry 34 relative to the subject 14. As discussed above, the gantry 34 may move axially along a long axis 14L of the subject 14 in the direction of arrow 44, rotate in the direction of arrow 40, move perpendicular to the long axis 14L, and/or orthogonal to the axis 14L in the direction of arrow 42. Accordingly, the selection of a position for the first energy projection in block 314 may include positioning the source 36 relative to the subject 14 in any appropriate position. For example, it may be desired to acquire image data for imaging and/or reconstructing a model of a selected portion of the subject, such as a selected vertebrae. One skilled will understand, therefore, positioning the imaging system for acquiring the first energy projection may include positioning the imaging system 16 relative to the subject 14 for acquiring a selected image.

After making the selection in block 314, the first filter may be moved into the broad spectrum beam in block 318. As discussed above the first filter 204 may be moved into the beam path 110 to produce the first filter beam 110b'. Thus the collection of image data with the first filter beam may proceed in block 322. After collecting the first image data with the first filter beam in block 322 a selection of a position for a second energy image projection may be made in block 326. As discussed above, the second energy image need not be collected, however, if collecting a second energy is selected a determination of a position may be made in block 326. The position may be a selected position made in a manner similar to that discussed above regarding the selection for the first energy projection in block 314. In various embodiments, for example, it may be selected to include a projection at the subject 14 that both of the energy, and, therefore, movement of the imaging system, such as the source 36 including the x-ray tube 100, may not occur. It is understood, however, that the source 36 may move such as rotating around the subject 14 and/or due to movement of the gantry 34 relative to the subject.

After selecting a position for the second energy projection in block 326 the second filter 260 may be moved into the beam 110a in block 330. After moving the filter into the beam 110a, the second filter beam 110b" may pass the filter assembly 200 for collection of image data as a second filter beam in block 334 may occur. Accordingly, image data may be collected at both of the energies with the post-filter beams 110b', 110b" by movement of the respective filters 204, 260 into the beam 110a. The single broad spectrum beam 110a may be filtered to generate or create either and/or both of the post-filter beams 110b', 110b". The post-filter beams 110b may also be referred to as partial or limited spectrum beams as they are limited or partial spectrums of the broad spectrum beam 110a.

After collection of the second filter beam image data in block 334, a determination of whether additional projections are needed may be made in block 338. If no additional projections are needed or selected, a NO path 342 may be followed to an end block 346. Ending in block 346 may include ending or collection projections with either of the filtered beams 110b', 110b". However, it is understood that additional processes may occur, such as reconstruction of a selected model, performing of a procedure on the subject 14, or other appropriate post-imaging processes may occur.

If addition projections are selected in block 338, a YES path 350 may be followed. The YES path 350 may allow for a selection of acquiring either or both of image projection with the first or second filtered beam. As discussed above, the filter assembly 200 may also include open or blanks areas 210a in the filter carrier. Thus, the full or broad spectrum beam 110a may also be used to collect image data, if selected. It is understood, therefore, that a broad spectrum image may also be collected at block 351. It is understood, however, that a broad spectrum image is optional.

After determination and/or collection of the optional broad spectrum image collection, a first filter beam path 354 may be followed to select a position of the first energy image projection in block 314 to continue or loop the process.

Accordingly, either only the first energy image projection may be collected and/or both the first and second energy projection may be collected.

In addition and/or alternatively thereto, however, a second filtered beam path 358 may also be followed. The second filtered beam path 358 may move to selecting a position for the second energy image projection in block 326. Again, as discussed above, image data may be collected at either or both of the first or second energy and/or other additional energies, and/or need not be collected at all of the selected energies. Thus, the YES path 350 may include collecting images at any selected energy and/or broad spectrum energies, as illustrated above.

The imaging system 16 including the single x-ray beam source 100 may emit a broad spectrum beam 110a. Selected filters, such as the first and second filters 204, 260 may filter the single broad spectrum beam 110a to two filtered or partial spectrum beams 110b', 110b". The two filtered beams 110b', 110b" may include energies that allow for collection of two different energy image projections for selected purposes, such as for distinguishing selected contrast agents, selected tissues, or other appropriate matter with distinguishable attenuation characteristics. Nevertheless, the imaging system 16 may include the filter assembly 200 to allow for generation of the two energy beams even if the x-ray source tube 100 of the source 36 only emits only a single broad spectrum initial or primary beam.

As discussed above, the imaging system 16 may be used to acquire image data of the subject 14 for reconstruction of a model thereof. Reconstructing a model of the subject 14 may include using a plurality of projections acquired with the imaging system 16 to generate a 3D model of the subject 14. Image data, therefore, acquired relative to the subject 14 at a plurality of positions and/or over a period of time may be used to reconstruct the model, such as the model 18 for display on the display device 20. The reconstruction may occur as discussed above. In various embodiments, however, a reconstruction of the model 18 for display may be based upon various types of image data acquired of the subject 14. As discussed above, dual energy image data may be acquired of the subject 14. In addition to and/or alternatively to, a low dose or lower dose image acquisition technique may be used to acquire image data of the subject 14 for performing the 3D reconstruction. In various embodiments, for example, the source 36 may be positioned at various positions relative to the subject 14 and acquisition of image projections may be made at the different positions that are used for the reconstruction. The reconstruction, therefore, is based upon the plurality of projections. In various embodiments, each of the projections may be at a single or selected dose, such as with a different spectra of energy. Thus, the x-ray does to the subject 14 may be limited, as opposed to acquire all image data with the broad spectrum, by about 10% to about 60%.

Figure 5:
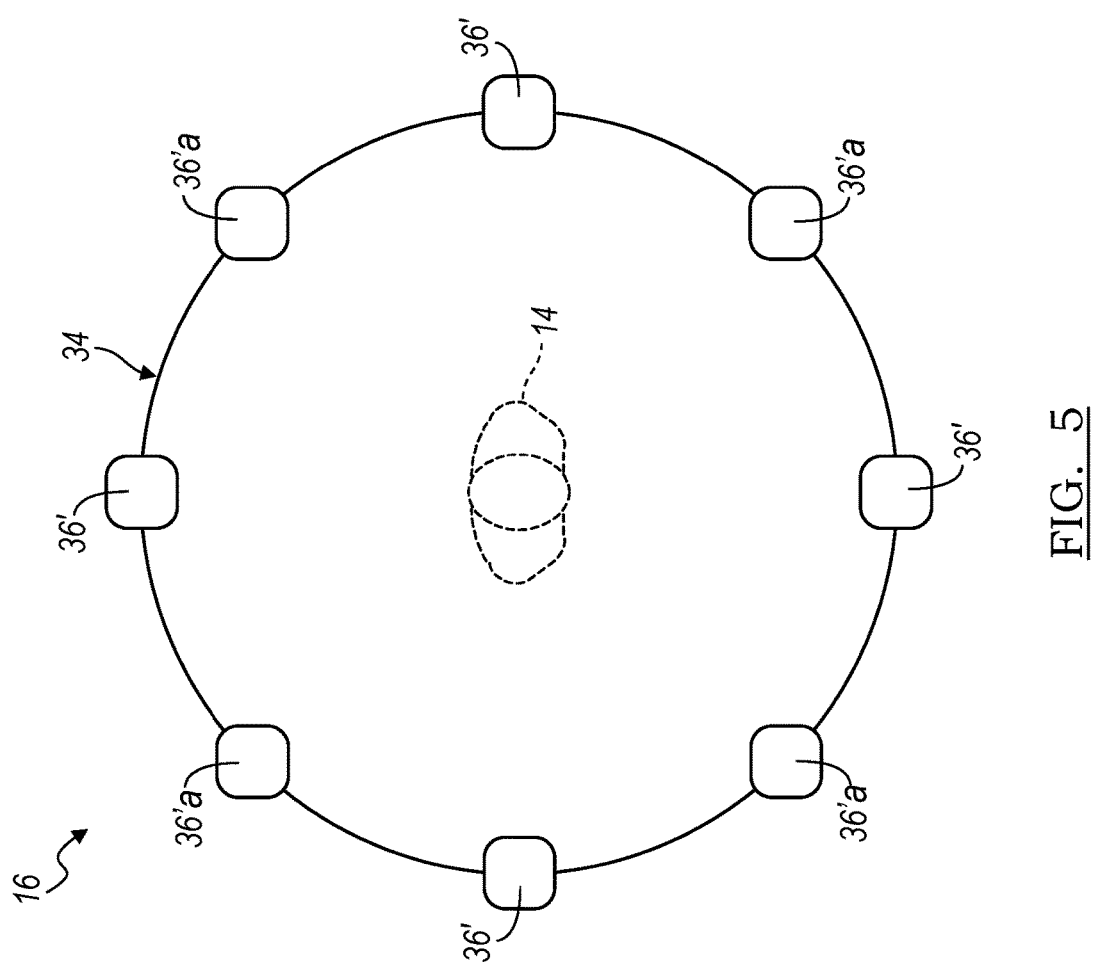
FIG. 5 is a schematic illustration of an imaging system including a source assembly, according to various embodiments.

The acquisition of image data of the subject for performing a reconstruction to generate a three-dimensional image may, for example, include acquiring projection at selected intervals around the subject 14. With reference to FIG. 5, the imaging system 16 is schematically illustrated. The imaging system 16 may include the source 36' that is moved within and/or relative to the gantry 34. It is understood that the detector 38 may also move relative to the source 36 for acquisition of image projections of the subject 14. Accordingly, while the FIG. 5 schematically illustrates the gantry 34 and the source 36', it is understood that the detector and other portions of the imaging system 16 may also be present. Nevertheless, the source 36' may move around a circle, or other appropriate shape relative to the subject 14, with the imaging system 16. As illustrated in FIG. 5, for example, the source 36' may move to various selected positions, any number of positions may be selected and the eight illustrated positions are only exemplarily. It is understood, however, that the source 36' may move to any appropriate number of positions to acquire projections of the subject 14 to ensure adequate data collection for performing the image reconstructions.

In various embodiments, for example, the imaging system 16 may be operated, such as by the controller 32 based upon input by the user 12, or other appropriate input, to move the source 36 relative to the subject 14 in the exemplary eight positions (or other appropriate positions) illustrated in FIG. 5. At each of the positions the source 26 may emit high power or a selected power of x-rays that are detected at a detector for acquisition of image projections of the subject 14. The image projections may allow for reconstruction of a selected image, such as a three-dimensional model, of the subject 14.

In various embodiments, however, the eight positions of the source 36 may be used to acquire projections of the subject 14 at different or varying intensities of the x-rays beam. In various embodiments, the filter assembly 200 may be used in the source 36 to alter a power of the beam emitted by the x-ray tube 100 through the subject 14. In various embodiments, for example, with reference to FIGS. 6A and 6B, the source assembly 36' may include a filter assembly 200', similar to the filter assembly 200 as discussed above. The filter assembly 200' may include the first filter 204 and an open or unfiltered portion 400. The open portion 400 may be an opening or void in the filter carrier 210. As discussed above the x-ray tube or tube 100 may emit a pre-filter beam 110a. The pre-filter beam may be filtered by the first filter 204 to be a filter beam 110b. The first filter 604 may filter the pre-filter beam 110a to be a low energy post filter beam 110b.

Figure 6A:
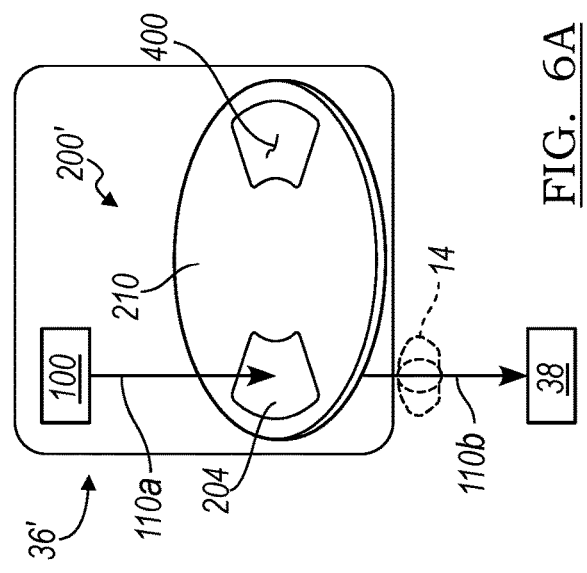
FIGS. 6A and 6B are schematic illustrations of an imaging system with a filter assembly in different configurations, according to various embodiments.

Turning reference to FIG. 6A, the filter assembly 200' may rotate or move the filter carrier 210 such that the filter 204 is moved out of the beam 110 and the void 400 is moved into the beam 110a. The source assembly 26'a, therefore, may include the void 400 positioned within the beam 110a. In this position or configuration, therefore, the source assembly 36'a may be used to emit a full power beam such that the beam after passing the filter carrier 210 is the same power and unfiltered. Thus, the full beam power that is emitted by the tube 100 may pass through the subject or interact with the subject 14 and be detected at the detector 38.

Figure 6B:
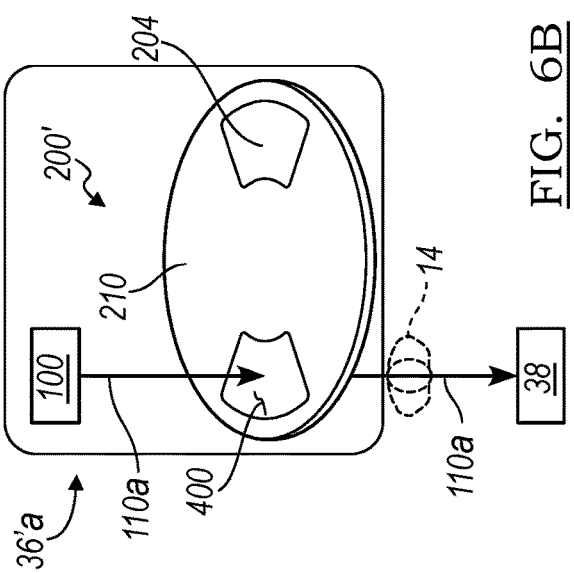

Returning reference to FIG. 5 and with continuing reference to FIGS. 6A and 6B, the imaging system 16 may acquire image projections of the subject 14 at different powers or different attenuations at different positions relative to the subject 14. For example, as illustrated at FIG. 6A, the source assembly 36 may be configured as the source assembly 36' such that the filter 204 is positioned in the beam 110a to filter or reduce a power of the beam as it passes through the subject 14 or it interacts with the subject 14. At the positions of the source 36'a, the source assembly 36'a may include an unfiltered beam, thus being configured to allow an unfiltered beam to pass from the source tube 100 and interact with the subject 14. As illustrated in FIG. 5, the source assembly 36 may be configured to alternatively change or alternate between the high power and low power beam that reaches the subject 14. As illustrated in FIG. 5, the imaging system 16 may ease the single source tube 100 to alter a power of the x-rays reaching the subject 14.

The imaging system 16 with the source assembly 36 may be configured into at least two configurations, including the configuration 36', as illustrated in FIG. 6A, and the configuration 36'a, as illustrated in FIG. 6B. The x-ray tube 100 may emit the beam 110a. In the first or filtered configuration the first filter 204 may filter the beam 110a such that the source assembly 36 emits the filtered beam 110b. The filtered beam 110b may be a low power beam and/or different spectra that reaches the subject 14. The low power beam 110b may include selected power characteristics such as kVp and amount of beam filtration.

The source assembly 36'a configuration may include an unfiltered region 400 of the filter carrier 210 and/or filter assembly 200 such that the emitted beam 110a emits or leaves the source assembly 36'a and reaches the subject 14 at a full or first power. Thus, the source assembly 36'a may allow for an emission of a high power radio beam to reach the subject 14.

As illustrated above, therefore, the single source assembly 36 including the single source tube 100 may be used to emit a beam at a high power or first power 110a and a second or low power 110b. As illustrated in FIG. 5 the source assembly 36 may be changed between configurations in alternating positions or to acquire alternating frames of image projections of the subject 14. Thus, the imaging system 16 may be used to acquire image projections of the subject 14 at two different powers at different positions.

The low power beam 110b may allow for acquisition of image projections of the subject 14 at a lower power than the higher full power beam 110a. Thus, when alternating the configuration of the source assembly 36, as illustrated in FIG. 5, a selected set of image projections may be acquired of the subject 14 at a lower dose than if all of the projections were acquired at the higher full dose. As exemplary illustrated in FIG. 5, a full set of projections may be acquired of the subject 14 at a selected reduction of power. Thus, the x-ray does to the subject 14 may be limited, as opposed to acquire all image data with the broad spectrum, by about 10% to about 60%.

The total selected projections acquired for a reconstruction, therefore, may be done at a total lower dose (e.g. of x-rays) to the subject 14 due to the low power acquisitions at 36' at the positions as illustrated in FIG. 5. The high dose projections 36'a allow for a high signal to noise ratio for reconstructing a model of the subject 14. The low power projections may have a lower signal to noise ratio, but provide appropriate data for assisting in the reconstruction of the model 18 of the subject 14. For example, the low power projections may allow for an identification of edges of various features, such as bony or high attenuation structures, of the subject 14. Accordingly, while a high signal to noise ratio may not be achieved with a low powered projection, selected information may be acquired for assisting in a reconstruction. Interpolation may be made between the high and low powered projections to assist in the reconstruction. The reconstruction, therefore, may use the low power projections, even though a lower signal to noise ratio may be achieved, to perform the reconstruction.

Various reconstruction techniques may be used to construct the model 18 of the subject 14, even with the lower signal to noise ratio image projections. The lower signal to noise ratio projections may also be referred to as noisy projections, even though they include selected data.

Various reconstruction techniques may include, to perform a reconstruction, for example, a machine learning system. The machine learning system may be trained to identify features in the high noise projections to assist in defining the reconstruction using the sparse data collection technique including the selected or alternating high energy or high dose projections. The low dose projections may allow for or generate a sparse image acquisition or data acquisition of the subject 14, with a selected reconstruction techniques may be used to textualize the sparse data, such as identifying edges within the low dose projections. The high does projections may be used to identify spatial resolution and to perform the reconstruction and a low loss reconstruction may be provided with the high noise projections used to interpolate or assist in the reconstruction method. Thus, the x-ray does to the subject 14 may be limited, as opposed to acquire all image data with the broad spectrum, by about 10% to about 60%.

Figure 7:
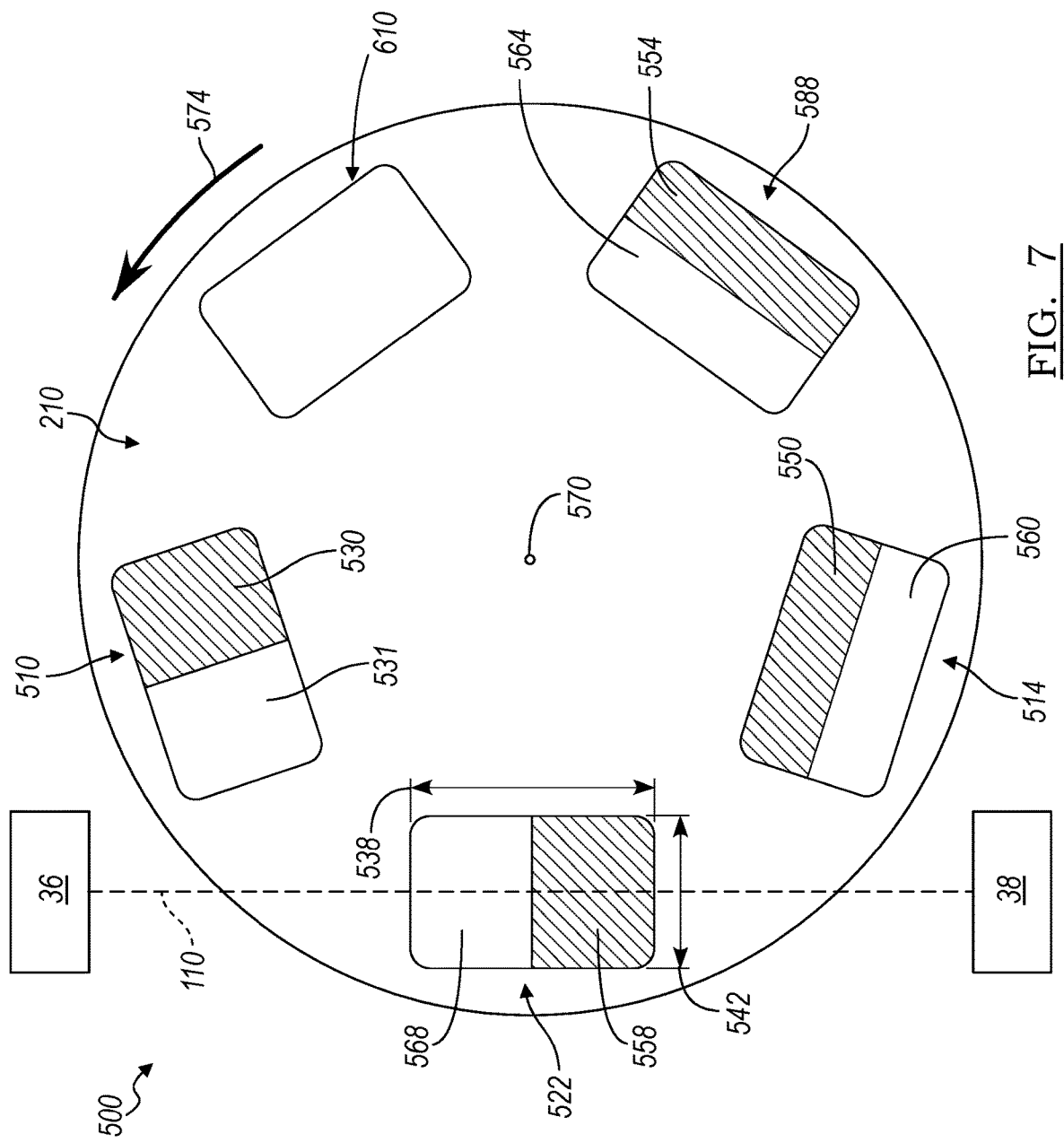
FIG. 7 is a schematic illustration of a filter assembly, according to various embodiments.

In various embodiment, the imaging system 16 including the filter assembly 200, as discussed above, may include additional or alternative filter members such as those included in a filter system 500 as illustrated in FIG. 7. The filter system 200 may include a filter carrier 210', similar to the filter carrier 210, as discussed above. The filter carrier 210' may be driven by various assemblies and portions, including those as discussed above, such as the motor or motor assembly 302 that may be driven directly and/or via various belts as discussed above. Nevertheless, the filter carrier 210 may rotate relative to the source 36 and the detector 38. The source 36 may emit a beam along the beam path 110. The beam emitted by the source 36 may pass through a portion of the filter carrier 210 and reach and/or be blocked or filtered by the filter portion on the filter carrier 210.

In various embodiments, the filter carrier may carry or move one or more filter portions. The filter carrier 210 may hold a first filter portion 510, a second filter portion 514, a third filter portion 518, and a fourth filter portion 522. Each of the filter portions may be similar to one another, but include varying sections, as discussed further herein, that may block a portion or region of the beam 110. In various embodiments, for example, each of the filter portions 510, 514, 518, 522 may be provided to assist in detecting and/or correcting for scattering of the beam 110 between the source 36 and the detector 38. The beam 110 may be an x-ray beam that is emitted by a tube, such as the tube 100, and the source 36. The x-ray beam may pass through or relative to the filter carrier 210 to the detector 38 and be detected for generating an image projection of the subject, such as the subject 14. The beam 110a, however, may be scattered by various interactions, including air or other material interactions.

Each of the filter sections 510-522, may include different or selected configurations. For example, the filter section in 510 may include a filter or blocking portion 530 and an opening or blank portion 534. The blocking section 530 may include a portion that substantially or entirely blocks the beam 110a from passing through the filter section 510 toward the detector 38. The blocking section 530 may, for example, include a high density x-ray blocking material such as lead, or other appropriate materials. The void 534 may be substantially open, such as an air void or opening positioned relative to the blocking portion 530. The filtering section 510 may include a selected dimension, such as a first dimension 538 and a second dimension 542. The dimensions 538, 542 may generally be known or consistent for each section or portion that a projection may be acquired of the subject 14 at the detector 38. Accordingly, the filter carrier 210' may also be formed of a substantially blocking material such that the beam 110a passes substantially only through the filter portions, including the void 534 of the filter portion 510.

The filter carrier 210, as discussed above, may include a selected number, such as four of the filter regions including the filter region 510, the filter region 514, the filter region 518, and the filter region 522. Each of the filter regions may include substantially blocking portions, such as the blocking portions 550, 554, and 558 of the respective filter regions 514, 518, 522. Each of the filter regions may also include respective void or opening portions 560, 564, and 568 of the respective filter regions 514, 518, 522. Accordingly, each of the filter regions may include substantially blocking regions 530, 550, 554, and 558 and respective open or void regions 534, 560, 564, and 568.

Each of the filter regions 510, 514, 518, 522 may be positioned relative to the beam 110. As illustrated in FIG. 7, the respective void and blocking portions that are positioned within the beam 110 may allow for defining or passing the beam through different blocking portions relative to void portions to identify or block selected halves, allowing for defining quadrants of the detector 38. As illustrated in FIG. 7, as the filter carrier 210 rotates around a center point 570 in a selected direction, such as generally in the direction of 574, each of the filter regions 510, 514, 518, 522 pass through the beam 110. Each of the filter regions including the blocking portions allow for blocking one-half of the detector space or surface. As each of the four blocking regions or filter regions pass through the beam 110, therefore, quadrants may be defined on the detector 38. The blocking regions positioned relative to the opening or void regions allow for imaging or defining scattering portions of the beam 110.

Figure 8:
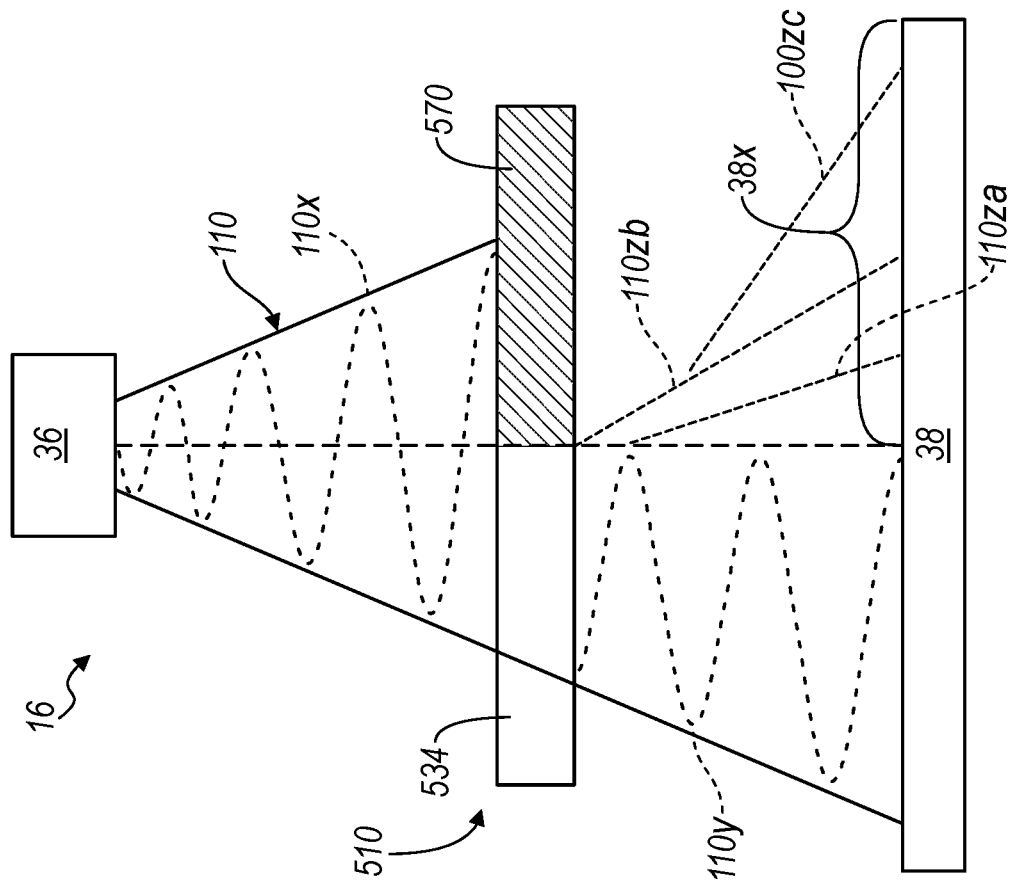
FIG. 8 is a schematic illustration of an imaging system, according to various embodiments.

With continuing reference to FIG. 7 and additional reference to FIG. 8, the filter region 510 is illustrated, as an example. The filter region 510, as discussed above, includes the void portion 534 and the blocking portion 530. The source 36 may emit the beam 110 past the filter region 510 and toward the detector 38. As illustrated in FIG. 8, the blocking region 530 blocks a portion of the beam 110 such as substantially about one-half of the beam 110, including the blocked beam portion 110x. The open or blade portion 534 allows for the beam 110 to pass and allows for a passing or unblocked beam portion 110y.

As illustrated in FIG. 8, the beam 110 may be split or at least partially partitioned between the blocked portion 110x and the passing or through portion 110y. The passing portion 110y, and also referred to as a partial beam, may contact the detector 38 to generate or allow for a projection to be produced of the passing portion 110y. The blocked portion 110x, however, is generally blocked from reaching the detector 38. As illustrated in FIG. 8, the filter region 510, including the through or void portion 534 and the blocking filter 530, allows for the separation of the beam 110 into the blocked portion 110x and the passing portion 110y. As discussed above, the filter carrier 210 may include a selected number of portions, such as the four filter void regions or portions 510, 514, 518, 522 to allow for generation or selection of different blocked portions of the beam 110 and the blocking portion or filter portion 510 as illustrated in FIG. 8 is merely exemplary.

The filter region 510, including the other filter regions as discussed above, including the blocking portion 530 generally blocks at least a portion of the detector 38 from the beam 110. The beam 110, however, may have an amount of scattering due to various interactions of portions of the beam 110, portions interacted or reached by the beam 110 or other factors. In various embodiments or under various condition, therefore, the beam 110 may have scattering such that all of the rays, such as x-rays in the beam 110, do not travel on a straight path from the source 36 to the detector 38. The scattering may be detected and/or determined as discussed herein.

As illustrated in FIG. 8, for example, the beam or portions of the beam passing through the void region 534 may be scattered due to various interaction from a path directly or straight from the source 36 to the detector 38. The portion of the beam 110 that passes substantially straight from the source 36 to the detector 38 may generally pass along or in the region of the unblocked beam 110y. Portions of the beam that pass through the void region 534 may be scattered for various reasons. As illustrated in FIG. 8, therefore, exemplary scattered portions of the beam may include scattered portions 110za, zb, zc. The scattered portion(s) 110za, zb, zc may contact the detector 38 in a generally blocked region or area 38x, which may also be referred to as an occluded portion or region. The blocked region 38x may generally be a region of the detector 38 that is blocked due to the blocking region 530 of the filter region or portion 510. Accordingly, any detection in the blocked region 38 would generally be due to scattering 110za, zb, zc of the beam 110. The scattered beam portion 110za, zb, zc may interact or reach the detector 38 in the blocked region 38x. It is understood that different positions of the blocking portion, such as the blocking portion 530 including the blocking portions 550, 554, and 558, as discussed above, may produce or allow for a determination of different scattering regions or portions.

Figure 9:
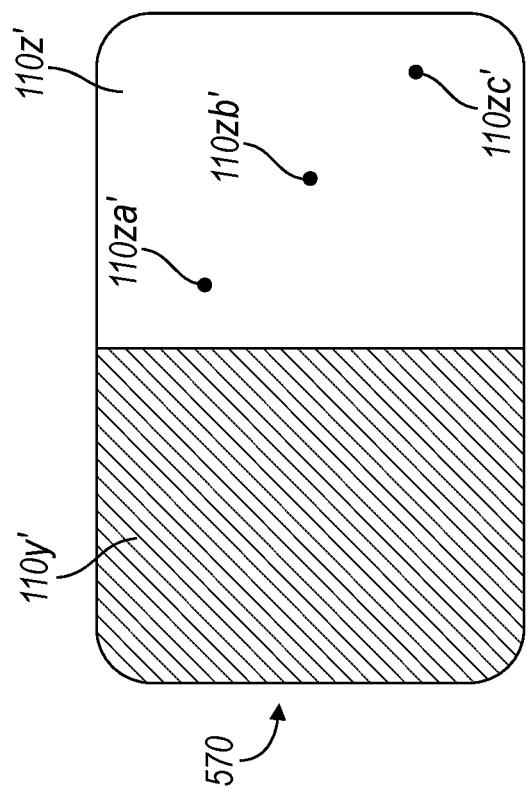
FIG. 9 is an exemplary illustration of a projection acquired with a selected filter configuration.

With continuing reference to FIG. 8, and reference to FIG. 9, scattered beam information (i.e. the detected portions on the detector 38 in the blocked region 38x) may be used to selectively determine and/or correct for scattering distortion and/or artifacts in image data. With reference to FIG. 9 an image data or projection 570 is illustrated. The imaged projection 570 may include an unblocked or beam projection portion 110y'. A blocked or non-image projection portion 110z' may also be included in the image data 570. As schematically illustrated in FIG. 9, the imaged projection 570 may include the unblocked region 110y' that include substantially an eradiation of the entire region of the detector 38 with the beam 110. As discussed above, the void region 534 may allow for a passage of the beam 110 to the detector 38 in the area 110y.

The projection at 570, however, will generally include a void or un-projected region due to the blocking of the detector 38 by the blocking region 530. Scattering, however, as discussed above, may allow fora scattering of portions of the beam 110za, zb, zc. Scattered portions of the beam 110y may produce selected detections on the detector 38 that may be detected for projection or image data 570. As exemplary illustrated in FIG. 9, the blocked portion may include scattered projection data 110za', 110zb', and 110zc'. It is understood that any appropriate or scattered amount of data may be detected at the detector 38 in the blocked region. Accordingly, the projection 570 may include more than the three scattered points, as illustrated in FIG. 9, which are included nearly for the example discussion herein.

The projection 570, acquired with a selected one of the filter regions, as discussed above, may be used for correction of image data collected with the imaging system 16. As discussed above, the various projection or blocking regions may be used to determine any appropriate division of the detector 38 for scattering image data or artifacts. The exemplary inclusion of the four projection regions or filter regions is merely exemplary. Nevertheless, each of the filter regions may allow for a determination of a selected amount of scattering relative to the detector 38 and the source 36.

The projection image 570, as exemplary illustrated in FIG. 9, can include the scattering image data. The scattered image data 110z' may be used for correction of image data collected with the imaging system 16. For example, any filter applied to the imaging system 16, even including a lower or partial filtering filter may allow for or include scatter image data. Accordingly, the scattering filter, including the scattering filter regions 510-522 as discussed above, may allow for collection of scattering projections, including that illustrated in FIG. 9 as the scattering image 570. Scattering images may be collected with the imaging system 16. The scattering images may then be used to subtract from the selected projection to allow for correction of scatter data and image projections. For example, as illustrated in FIG. 9, the scattered projection points 110za', 110zb', and 110zc' may be subtracted from selected image projections acquired with the imaging system 16. The scatter data may be subtracted to allow for reducing artifacts due to scattering when collecting image projections of the subject 14 with the imaging system 16. Also, the occluded portion 38x that may allow the acquisition of the image region 110z' may vary over time. That is, during the image data acquisition (i.e., projection acquisition) the filter may move over time to occlude a different portion of the detector 38. Thus, the occluded region or portion may vary or change with each acquisition, and each acquisition may change over time due to movement of the imaging system 16 and/or the filter portion 510. Thus, the position of the occluded portion created by the filter member 510 may be time varying with and relative to an acquisition time.

Accordingly, the imaging system 16 may include one or more filter portions that allow for filtering and selection of selected image projections collected with the imaging system 16. The filter portions may generate scattering image data or projections due to interactions of x-ray beams from the source 36 due to physical properties thereof and/or the environment through which the projection or beam passes. The scattering filters, such as the filter portions 510-522 may be moved into the beam 110 to assist and/or determine scattering of the beam 110 in the imaging system 16. The scattering filter or regions 510-522, therefore, may assist in determining or correcting for scattering as discussed above.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An imaging system configured to acquire image projections of a subject, comprising:
    a source configured to emit x-rays as a whole beam having a whole cross-section area;
    a filter assembly, including:
        a filter member configured to occlude at least a portion of the cross-section area of the whole beam to form a partial beam,
        a filter carrier configured to move the filter member relative to the whole beam to cause the filter member to occlude at least a portion of the whole beam to form the partial beam and move the filter member away from the whole beam to allow passage of the whole beam;
    a detector configured to detect the x-rays in the whole beam and the partial beam; and
    a control system configured to control the position of the filter member with the filter carrier to detect the whole beam or the partial beam;
    a correction system configured to execute instructions to:
        determine scatter of x-rays at least at the detector in the partial beam, and
        determine projection correction to correct for scattering of the x-rays.

2. The system of claim 1, further comprising:
    a reconstruction system configured to reconstruct the model of the subject with image data acquired with the whole beam based on the determined projection correction.

3. The system of claim 1, wherein the first member includes a first filter member and a second filter member;
    wherein the first filter member occludes a first portion of the whole beam to form a first partial beam and the second filter member occludes a second portion of the whole beam to form a second partial beam.

4. The system of claim 3, wherein the first partial beam is detected at the detector to determine a first scattering in a first detector region and the second partial beam is detected at the detector to determine a second scattering in a second detector region.

5. The system of claim 4, wherein the filter system further includes a third filter member and a fourth filter member;

wherein the third filter member occludes a third portion of the whole beam to form a third partial beam and the fourth filter member occludes a fourth portion of the whole beam to form a fourth partial beam.

6. The system of claim 5, wherein the third partial beam is detected at the detector to determine a third scattering in a third detector region and the fourth partial beam is detected at the detector to determine a fourth scattering in a fourth detector region.

7. The system of claim 6, wherein the first detector region, the second detector region, the third detector region, and the fourth detector region are configured to overlap to allow for determination of scattering in four quadrants of the detector.

8. The system of claim 1, wherein the filter member includes at least a first filter member, a second filter member, a third member, and a fourth filter member, wherein each of the first filter member, the second filter member, the third filter member, and the fourth filter member are configured to selectively occlude a different area of the whole cross-section area to form at least four different partial beams;
wherein the filter carrier further defines an open passage to allow the whole beam to pass and be detected at the detector.

9. A method of correcting for x-ray scattering, comprising:
emitting a whole beam of x-rays from a source having a whole cross-section area;
detecting the whole beam at a detector;
selectively occluding the whole beam with a filter member to occlude at least a portion of the cross-section area of the whole beam to form a partial beam,
detecting at the detector the partial beam; and
operating a processor module to execute instructions operable to:
determine a scatter of x-rays at least at the detector in the partial beam, and
determine a projection correction to correct for scattering of the x-rays.

10. The method of claim 9, wherein selectively occluding the whole beam with the filter member includes selectively occluding the whole beam with a first filter member to form a first partial beam and a second filter member to form a second partial beam.

11. The method of claim 9, further comprising:
detecting the partial beam at a first detector region that relates to the first partial beam cross-section area.

12. The method of claim 11, further comprising:
detecting a scattering of x-rays at an occluded region of the detector other than the first detector region when the first partial beam is detected;
wherein operating the processor module to execute instructions to determine the scatter of x-rays includes receiving the x-ray scattering image data.

13. The method of claim 12, wherein operating the processor module to execute instructions to determine the projection correction operable to correct for scattering of the x-rays includes removing scattered x-ray image data from image data based on a projection acquired with the whole beam.

14. The method of claim 13, further comprising:
generating a reconstruction based on the determined projection correction.

15. A method of correcting for x-ray scattering in an image reconstruction, comprising:
detecting a plurality of whole projections at a detector based on a whole beam of x-rays;
detecting a plurality of partial projections at the detector based on a partial beam of x-rays, wherein the partial beam is a portion of the whole beam that is configured to pass an occlusion formed by a filter member;
detecting a plurality of scatter x-ray projections at an occluded portion of the detector, wherein the occluded portion is the portion of the detector configured to be occluded by the filter member; and
operating a processor module to execute instructions operable to determine a projection correction in the plurality of whole projections to correct for scattering of the x-rays in the detected plurality of scatter x-ray projections.

16. The method of claim 15, further comprising:
forming the partial beam by selectively occluding the whole beam with the filter member to occlude at least a portion of a cross-section area of the whole beam.

17. The method of claim 15, wherein detecting the plurality of scatter x-ray projections at the occluded portion of the detector includes acquiring image data at a selected acquisition time;
where the position of the occluded portion created by the filter member is time varying with an acquisition time.

* * * * *

UNITED STATES PATENT AND TRADEMARK OFFICE
CERTIFICATE OF CORRECTION

PATENT NO. : 11,324,463 B1  
APPLICATION NO. : 17/080423  
DATED : May 10, 2022  
INVENTOR(S) : Patrick A. Helm et al.

Page 1 of 2

It is certified that error appears in the above-identified patent and that said Letters Patent is hereby corrected as shown below:

On the Title Page

Column 1, Line 1, After "2020", insert --¶(65) Prior Publication Data
US 2022/0125394 A1 Apr. 28, 2022--

In the Drawings

Sheet 3 of 7, Fig. 3A, Line 1, delete "110'b" and insert --110'-- therefor

Sheet 3 of 7, Fig. 3B, Line 1, delete "110"b" and insert --110b"--

In the Specification

Column 3, Line 10, delete "processor" and insert --processing-- therefor

Column 6, Line 9, delete "24," and insert --26,-- therefor

Column 8, Line 9, delete "210" and insert --204-- therefor

Column 9, Line 6, delete "210" and insert --240-- therefor

Column 9, Line 15, delete "306" and insert --302-- therefor

Column 9, Line 16, delete "210" and insert --240-- therefor

Column 9, Line 18, delete "306" and insert --302-- therefor

Column 9, Line 24, delete "200" and insert --204-- therefor

Column 9, Line 27, delete "210" and insert --240-- therefor

Signed and Sealed this  
Fourth Day of October, 2022

Katherine Kelly Vidal  
*Director of the United States Patent and Trademark Office*

CERTIFICATE OF CORRECTION (continued)
U.S. Pat. No. 11,324,463 B1

Column 9, Line 33, delete "210," and insert --240,-- therefor

Column 9, Line 45, delete "200" and insert --204-- therefor

Column 14, Line 16, delete "26" and insert --36-- therefor

Column 14, Line 36, delete "604" and insert --204-- therefor

Column 14, Line 42, delete "26'*a*," and insert --36'a,-- therefor

Column 16, Line 19, delete "200" and insert --500-- therefor

Column 18, Line 21, delete "38" and insert --38x-- therefor

Column 18, Line 47, delete "fora" and insert --for a-- therefor